United States Patent
Park et al.

(10) Patent No.: US 8,826,200 B2
(45) Date of Patent: Sep. 2, 2014

(54) ALTERATION FOR WAFER INSPECTION

(71) Applicant: KLA-Tencor Corporation, Milpitas, CA (US)

(72) Inventors: Allen Park, San Jose, CA (US); Ellis Chang, Saratoga, CA (US)

(73) Assignee: KLA-Tencor Corp., Milpitas, CA (US)

(*) Notice: Subject to any disclaimer, the term of this patent is extended or adjusted under 35 U.S.C. 154(b) by 0 days.

(21) Appl. No.: 13/893,267

(22) Filed: May 13, 2013

(65) Prior Publication Data

US 2013/0318485 A1    Nov. 28, 2013

Related U.S. Application Data

(60) Provisional application No. 61/652,052, filed on May 25, 2012.

(51) Int. Cl.
*G06F 17/50* (2006.01)

(52) U.S. Cl.
USPC .......................................................... 716/102

(58) Field of Classification Search
USPC .......................................................... 716/102
See application file for complete search history.

(56) References Cited

U.S. PATENT DOCUMENTS

| | | | |
|---|---|---|---|
| 3,495,269 A | 2/1970 | Mutschler et al. |
| 3,496,352 A | 2/1970 | Jugle |
| 3,909,602 A | 9/1975 | Micka |
| 4,015,203 A | 3/1977 | Verkuil |
| 4,247,203 A | 1/1981 | Levy et al. |
| 4,347,001 A | 8/1982 | Levy et al. |
| 4,378,159 A | 3/1983 | Galbraith |
| 4,448,532 A | 5/1984 | Joseph et al. |
| 4,475,122 A | 10/1984 | Green |
| 4,532,650 A | 7/1985 | Wihl et al. |
| 4,555,798 A | 11/1985 | Broadbent, Jr. et al. |
| 4,578,810 A | 3/1986 | MacFarlane et al. |
| 4,579,455 A | 4/1986 | Levy et al. |
| 4,595,289 A | 6/1986 | Feldman et al. |
| 4,599,558 A | 7/1986 | Castellano, Jr. et al. |
| 4,633,504 A | 12/1986 | Wihl |

(Continued)

FOREIGN PATENT DOCUMENTS

| | | |
|---|---|---|
| CN | 1339140 | 3/2002 |
| CN | 1398348 | 2/2003 |

(Continued)

OTHER PUBLICATIONS

U.S. Appl. No. 60/681,095, filed May 13, 2005 by Nehmadi et al.

(Continued)

*Primary Examiner* — Jack Chiang
*Assistant Examiner* — Brandon Bowers
(74) *Attorney, Agent, or Firm* — Ann Marie Mewherter (57) ABSTRACT

Methods and systems for binning defects on a wafer are provided. One method includes identifying areas in a design for a layer of a device being fabricated on a wafer that are not critical to yield of fabrication of the device and generating an altered design for the layer by eliminating features in the identified areas from the design for the layer. The method also includes binning defects detected on the layer into groups using the altered design such that features in the altered design proximate positions of the defects in each of the groups are at least similar.

21 Claims, 3 Drawing Sheets

(56) References Cited

U.S. PATENT DOCUMENTS

| | | |
|---|---|---|
| 4,641,353 A | 2/1987 | Kobayashi |
| 4,641,967 A | 2/1987 | Pecen |
| 4,734,721 A | 3/1988 | Boyer et al. |
| 4,748,327 A | 5/1988 | Shinozaki et al. |
| 4,758,094 A | 7/1988 | Wihl et al. |
| 4,766,324 A | 8/1988 | Saadat et al. |
| 4,799,175 A | 1/1989 | Sano et al. |
| 4,805,123 A | 2/1989 | Specht et al. |
| 4,812,756 A | 3/1989 | Curtis et al. |
| 4,814,829 A | 3/1989 | Kosugi et al. |
| 4,817,123 A | 3/1989 | Sones et al. |
| 4,845,558 A | 7/1989 | Tsai et al. |
| 4,877,326 A | 10/1989 | Chadwick et al. |
| 4,926,489 A | 5/1990 | Danielson et al. |
| 4,928,313 A | 5/1990 | Leonard et al. |
| 5,046,109 A | 9/1991 | Fujimori et al. |
| 5,124,927 A | 6/1992 | Hopewell et al. |
| 5,189,481 A | 2/1993 | Jann et al. |
| 5,355,212 A | 10/1994 | Wells et al. |
| 5,444,480 A | 8/1995 | Sumita |
| 5,453,844 A | 9/1995 | George et al. |
| 5,481,624 A | 1/1996 | Kamon |
| 5,485,091 A | 1/1996 | Verkuil |
| 5,497,381 A | 3/1996 | O'Donoghue et al. |
| 5,528,153 A | 6/1996 | Taylor et al. |
| 5,544,256 A | 8/1996 | Brecher et al. |
| 5,563,702 A | 10/1996 | Emery et al. |
| 5,572,598 A | 11/1996 | Wihl et al. |
| 5,578,821 A | 11/1996 | Meisberger et al. |
| 5,594,247 A | 1/1997 | Verkuil et al. |
| 5,608,538 A | 3/1997 | Edgar et al. |
| 5,619,548 A | 4/1997 | Koppel |
| 5,621,519 A | 4/1997 | Frost et al. |
| 5,644,223 A | 7/1997 | Verkuil |
| 5,650,731 A | 7/1997 | Fung et al. |
| 5,661,408 A | 8/1997 | Kamieniecki et al. |
| 5,689,614 A | 11/1997 | Gronet et al. |
| 5,694,478 A | 12/1997 | Braier et al. |
| 5,696,835 A | 12/1997 | Hennessey et al. |
| 5,703,969 A | 12/1997 | Hennessey et al. |
| 5,737,072 A | 4/1998 | Emery et al. |
| 5,742,658 A | 4/1998 | Tiffin et al. |
| 5,754,678 A | 5/1998 | Hawthorne et al. |
| 5,767,691 A | 6/1998 | Verkuil |
| 5,767,693 A | 6/1998 | Verkuil |
| 5,771,317 A | 6/1998 | Edgar |
| 5,773,989 A | 6/1998 | Edelman et al. |
| 5,774,179 A | 6/1998 | Chevrette et al. |
| 5,795,685 A | 8/1998 | Liebmann et al. |
| 5,822,218 A | 10/1998 | Moosa et al. |
| 5,831,865 A | 11/1998 | Berezin et al. |
| 5,834,941 A | 11/1998 | Verkuil |
| 5,852,232 A | 12/1998 | Samsavar et al. |
| 5,866,806 A | 2/1999 | Samsavar et al. |
| 5,874,733 A | 2/1999 | Silver et al. |
| 5,884,242 A | 3/1999 | Meier et al. |
| 5,889,593 A | 3/1999 | Bareket |
| 5,917,332 A | 6/1999 | Chen et al. |
| 5,932,377 A | 8/1999 | Ferguson et al. |
| 5,940,458 A | 8/1999 | Suk |
| 5,948,972 A | 9/1999 | Samsavar et al. |
| 5,955,661 A | 9/1999 | Samsavar et al. |
| 5,965,306 A | 10/1999 | Mansfield et al. |
| 5,978,501 A | 11/1999 | Badger et al. |
| 5,980,187 A | 11/1999 | Verhovsky |
| 5,986,263 A | 11/1999 | Hiroi et al. |
| 5,991,699 A | 11/1999 | Kulkarni et al. |
| 5,999,003 A | 12/1999 | Steffan et al. |
| 6,011,404 A | 1/2000 | Ma et al. |
| 6,014,461 A | 1/2000 | Hennessey et al. |
| 6,040,912 A | 3/2000 | Zika et al. |
| 6,052,478 A | 4/2000 | Wihl et al. |
| 6,060,709 A | 5/2000 | Verkuil et al. |
| 6,072,320 A | 6/2000 | Verkuil |
| 6,076,465 A | 6/2000 | Vacca et al. |
| 6,078,738 A | 6/2000 | Garza et al. |
| 6,091,257 A | 7/2000 | Verkuil et al. |
| 6,091,846 A | 7/2000 | Lin et al. |
| 6,097,196 A | 8/2000 | Verkuil et al. |
| 6,097,887 A | 8/2000 | Hardikar et al. |
| 6,104,206 A | 8/2000 | Verkuil |
| 6,104,835 A | 8/2000 | Han |
| 6,117,598 A | 9/2000 | Imai |
| 6,121,783 A | 9/2000 | Horner et al. |
| 6,122,017 A | 9/2000 | Taubman |
| 6,122,046 A | 9/2000 | Almogy |
| 6,137,570 A | 10/2000 | Chuang et al. |
| 6,141,038 A | 10/2000 | Young et al. |
| 6,146,627 A | 11/2000 | Muller et al. |
| 6,171,737 B1 | 1/2001 | Phan et al. |
| 6,175,645 B1 | 1/2001 | Elyasaf et al. |
| 6,184,929 B1 | 2/2001 | Noda et al. |
| 6,184,976 B1 | 2/2001 | Park et al. |
| 6,191,605 B1 | 2/2001 | Miller et al. |
| 6,201,999 B1 | 3/2001 | Jevtic |
| 6,202,029 B1 | 3/2001 | Verkuil et al. |
| 6,205,239 B1 | 3/2001 | Lin et al. |
| 6,215,551 B1 | 4/2001 | Nikoonahad et al. |
| 6,224,638 B1 | 5/2001 | Jevtic et al. |
| 6,233,719 B1 | 5/2001 | Hardikar et al. |
| 6,246,787 B1 | 6/2001 | Hennessey et al. |
| 6,248,485 B1 | 6/2001 | Cuthbert |
| 6,248,486 B1 | 6/2001 | Dirksen et al. |
| 6,259,960 B1 | 7/2001 | Inokuchi |
| 6,266,437 B1 | 7/2001 | Eichel et al. |
| 6,267,005 B1 | 7/2001 | Samsavar et al. |
| 6,268,093 B1 | 7/2001 | Kenan et al. |
| 6,272,236 B1 | 8/2001 | Pierrat et al. |
| 6,282,309 B1 | 8/2001 | Emery |
| 6,292,582 B1 | 9/2001 | Lin et al. |
| 6,324,298 B1 | 11/2001 | O'Dell et al. |
| 6,344,640 B1 | 2/2002 | Rhoads |
| 6,363,166 B1 | 3/2002 | Wihl et al. |
| 6,373,975 B1 | 4/2002 | Bula et al. |
| 6,388,747 B2 | 5/2002 | Nara et al. |
| 6,393,602 B1 | 5/2002 | Atchison et al. |
| 6,407,373 B1 | 6/2002 | Dotan |
| 6,415,421 B2 | 7/2002 | Anderson et al. |
| 6,445,199 B1 | 9/2002 | Satya et al. |
| 6,451,690 B1 | 9/2002 | Matsumoto et al. |
| 6,459,520 B1 | 10/2002 | Takayama |
| 6,466,314 B1 | 10/2002 | Lehman |
| 6,466,315 B1 | 10/2002 | Karpol et al. |
| 6,470,489 B1 | 10/2002 | Chang et al. |
| 6,483,938 B1 | 11/2002 | Hennessey et al. |
| 6,513,151 B1 | 1/2003 | Erhardt et al. |
| 6,526,164 B1 | 2/2003 | Mansfield et al. |
| 6,529,621 B1 | 3/2003 | Glasser et al. |
| 6,535,628 B2 | 3/2003 | Smargiassi et al. |
| 6,539,106 B1 | 3/2003 | Gallarda et al. |
| 6,569,691 B1 | 5/2003 | Jastrzebski et al. |
| 6,581,193 B1 | 6/2003 | McGhee et al. |
| 6,593,748 B1 | 7/2003 | Halliyal et al. |
| 6,597,193 B2 | 7/2003 | Lagowski et al. |
| 6,602,728 B1 | 8/2003 | Liebmann et al. |
| 6,608,681 B2 | 8/2003 | Tanaka et al. |
| 6,614,520 B1 | 9/2003 | Bareket et al. |
| 6,631,511 B2 | 10/2003 | Haffner et al. |
| 6,636,301 B1 | 10/2003 | Kvamme et al. |
| 6,642,066 B1 | 11/2003 | Halliyal et al. |
| 6,658,640 B2 | 12/2003 | Weed |
| 6,665,065 B1 | 12/2003 | Phan et al. |
| 6,670,082 B2 | 12/2003 | Liu et al. |
| 6,680,621 B2 | 1/2004 | Savtchouk |
| 6,691,052 B1 | 2/2004 | Maurer |
| 6,701,004 B1 | 3/2004 | Shykind et al. |
| 6,718,526 B1 | 4/2004 | Eldredge et al. |
| 6,721,695 B1 | 4/2004 | Chen et al. |
| 6,734,696 B2 | 5/2004 | Horner et al. |
| 6,738,954 B1 | 5/2004 | Allen et al. |
| 6,748,103 B2 | 6/2004 | Glasser et al. |
| 6,751,519 B1 | 6/2004 | Satya et al. |
| 6,753,954 B2 | 6/2004 | Chen |
| 6,757,645 B2 | 6/2004 | Chang et al. |

(56) References Cited

U.S. PATENT DOCUMENTS

| | | | |
|---|---|---|---|
| 6,759,655 B2 | 7/2004 | Nara et al. |
| 6,771,806 B1 | 8/2004 | Satya et al. |
| 6,775,818 B2 | 8/2004 | Taravade et al. |
| 6,777,147 B1 | 8/2004 | Fonseca et al. |
| 6,777,676 B1 | 8/2004 | Wang et al. |
| 6,778,695 B1 | 8/2004 | Schellenberg et al. |
| 6,779,159 B2 | 8/2004 | Yokoyama et al. |
| 6,784,446 B1 | 8/2004 | Phan et al. |
| 6,788,400 B2 | 9/2004 | Chen |
| 6,789,032 B2 | 9/2004 | Barbour et al. |
| 6,803,554 B2 | 10/2004 | Ye et al. |
| 6,806,456 B1 | 10/2004 | Ye et al. |
| 6,807,503 B2 | 10/2004 | Ye et al. |
| 6,813,572 B2 | 11/2004 | Satya et al. |
| 6,820,028 B2 | 11/2004 | Ye et al. |
| 6,828,542 B2 | 12/2004 | Ye et al. |
| 6,842,225 B1 | 1/2005 | Irie et al. |
| 6,859,746 B1 | 2/2005 | Stirton |
| 6,879,403 B2 | 4/2005 | Freifeld |
| 6,879,924 B2 | 4/2005 | Ye et al. |
| 6,882,745 B2 | 4/2005 | Brankner et al. |
| 6,884,984 B2 | 4/2005 | Ye et al. |
| 6,886,153 B1 | 4/2005 | Bevis |
| 6,892,156 B2 | 5/2005 | Ye et al. |
| 6,902,855 B2 | 6/2005 | Peterson et al. |
| 6,906,305 B2 | 6/2005 | Pease et al. |
| 6,918,101 B1 | 7/2005 | Satya et al. |
| 6,919,957 B2 | 7/2005 | Nikoonahad et al. |
| 6,937,753 B1 | 8/2005 | O'Dell et al. |
| 6,948,141 B1 | 9/2005 | Satya et al. |
| 6,959,255 B2 | 10/2005 | Ye et al. |
| 6,966,047 B1 | 11/2005 | Glasser |
| 6,969,837 B2 | 11/2005 | Ye et al. |
| 6,969,864 B2 | 11/2005 | Ye et al. |
| 6,983,060 B1 | 1/2006 | Martinent-Catalot et al. |
| 6,988,045 B2 | 1/2006 | Purdy |
| 7,003,755 B2 | 2/2006 | Pang et al. |
| 7,003,758 B2 | 2/2006 | Ye et al. |
| 7,012,438 B1 | 3/2006 | Miller et al. |
| 7,026,615 B2 | 4/2006 | Takane et al. |
| 7,027,143 B1 | 4/2006 | Stokowski et al. |
| 7,030,966 B2 | 4/2006 | Hansen |
| 7,030,997 B2 | 4/2006 | Neureuther et al. |
| 7,053,355 B2 | 5/2006 | Ye et al. |
| 7,061,625 B1 | 6/2006 | Hwang et al. |
| 7,071,833 B2 | 7/2006 | Nagano et al. |
| 7,103,484 B1 | 9/2006 | Shi et al. |
| 7,106,895 B1 | 9/2006 | Goldberg et al. |
| 7,107,517 B1 | 9/2006 | Suzuki et al. |
| 7,107,571 B2 | 9/2006 | Chang et al. |
| 7,111,277 B2 | 9/2006 | Ye et al. |
| 7,114,143 B2 | 9/2006 | Hanson et al. |
| 7,114,145 B2 | 9/2006 | Ye et al. |
| 7,117,477 B2 | 10/2006 | Ye et al. |
| 7,117,478 B2 | 10/2006 | Ye et al. |
| 7,120,285 B1 | 10/2006 | Spence |
| 7,120,895 B2 | 10/2006 | Ye et al. |
| 7,123,356 B1 | 10/2006 | Stokowski et al. |
| 7,124,386 B2 | 10/2006 | Smith et al. |
| 7,133,548 B2 | 11/2006 | Kenan et al. |
| 7,135,344 B2 | 11/2006 | Nehmadi et al. |
| 7,136,143 B2 | 11/2006 | Smith |
| 7,152,215 B2 | 12/2006 | Smith et al. |
| 7,162,071 B2 | 1/2007 | Hung et al. |
| 7,171,334 B2 | 1/2007 | Gassner |
| 7,174,520 B2 | 2/2007 | White et al. |
| 7,194,709 B2 | 3/2007 | Brankner |
| 7,207,017 B1 | 4/2007 | Tabery et al. |
| 7,231,628 B2 | 6/2007 | Pack et al. |
| 7,236,847 B2 | 6/2007 | Marella |
| 7,271,891 B1 | 9/2007 | Xiong et al. |
| 7,379,175 B1 | 5/2008 | Stokowski et al. |
| 7,383,156 B2 | 6/2008 | Matsusita et al. |
| 7,386,839 B1 | 6/2008 | Golender et al. |
| 7,388,979 B2 | 6/2008 | Sakai et al. |
| 7,418,124 B2 | 8/2008 | Peterson et al. |
| 7,424,145 B2 | 9/2008 | Horie et al. |
| 7,440,093 B1 | 10/2008 | Xiong et al. |
| 7,570,796 B2 | 8/2009 | Zafar et al. |
| 7,676,077 B2 | 3/2010 | Kulkarni et al. |
| 7,683,319 B2 | 3/2010 | Makino et al. |
| 7,738,093 B2 | 6/2010 | Alles et al. |
| 7,739,064 B1 | 6/2010 | Ryker et al. |
| 7,760,929 B2 * | 7/2010 | Orbon et al. ................ 382/148 |
| 7,769,225 B2 | 8/2010 | Kekare et al. |
| 7,877,722 B2 * | 1/2011 | Duffy et al. ................... 716/55 |
| 7,890,917 B1 | 2/2011 | Young et al. |
| 7,904,845 B2 * | 3/2011 | Fouquet et al. ............... 716/136 |
| 7,968,859 B2 | 6/2011 | Young et al. |
| 8,041,103 B2 | 10/2011 | Kulkarni et al. |
| 8,073,240 B2 | 12/2011 | Fischer et al. |
| 8,112,241 B2 | 2/2012 | Xiong |
| 8,126,255 B2 | 2/2012 | Bhaskar et al. |
| 8,204,297 B1 | 6/2012 | Xiong et al. |
| 2001/0017694 A1 | 8/2001 | Oomori et al. |
| 2001/0019625 A1 | 9/2001 | Kenan et al. |
| 2001/0022858 A1 | 9/2001 | Komiya et al. |
| 2001/0043735 A1 | 11/2001 | Smargiassi et al. |
| 2002/0010560 A1 | 1/2002 | Balachandran |
| 2002/0019729 A1 | 2/2002 | Chang et al. |
| 2002/0026626 A1 | 2/2002 | Randall et al. |
| 2002/0033449 A1 | 3/2002 | Nakasuji et al. |
| 2002/0035461 A1 | 3/2002 | Chang et al. |
| 2002/0035641 A1 | 3/2002 | Kurose et al. |
| 2002/0035717 A1 | 3/2002 | Matsuoka |
| 2002/0088951 A1 | 7/2002 | Chen |
| 2002/0090746 A1 | 7/2002 | Xu et al. |
| 2002/0134936 A1 | 9/2002 | Matsui et al. |
| 2002/0144230 A1 | 10/2002 | Rittman |
| 2002/0145734 A1 | 10/2002 | Watkins et al. |
| 2002/0164065 A1 | 11/2002 | Cai et al. |
| 2002/0176096 A1 | 11/2002 | Sentoku et al. |
| 2002/0181756 A1 | 12/2002 | Shibuya et al. |
| 2002/0186878 A1 | 12/2002 | Hoon et al. |
| 2002/0192578 A1 | 12/2002 | Tanaka et al. |
| 2003/0004699 A1 | 1/2003 | Choi et al. |
| 2003/0014146 A1 | 1/2003 | Fujii et al. |
| 2003/0017664 A1 | 1/2003 | Pnueli et al. |
| 2003/0022401 A1 | 1/2003 | Hamamatsu et al. |
| 2003/0033046 A1 | 2/2003 | Yoshitake et al. |
| 2003/0048458 A1 | 3/2003 | Mieher et al. |
| 2003/0048939 A1 | 3/2003 | Lehman |
| 2003/0057971 A1 | 3/2003 | Nishiyama et al. |
| 2003/0076989 A1 | 4/2003 | Maayah et al. |
| 2003/0086081 A1 | 5/2003 | Lehman |
| 2003/0094572 A1 | 5/2003 | Matsui et al. |
| 2003/0098805 A1 | 5/2003 | Bizjak |
| 2003/0128870 A1 | 7/2003 | Pease et al. |
| 2003/0138138 A1 | 7/2003 | Vacca et al. |
| 2003/0138978 A1 | 7/2003 | Tanaka et al. |
| 2003/0169916 A1 | 9/2003 | Hayashi et al. |
| 2003/0173516 A1 | 9/2003 | Takane et al. |
| 2003/0192015 A1 | 10/2003 | Liu |
| 2003/0207475 A1 | 11/2003 | Nakasuji et al. |
| 2003/0223639 A1 | 12/2003 | Shlain et al. |
| 2003/0226951 A1 | 12/2003 | Ye et al. |
| 2003/0227620 A1 | 12/2003 | Hirokazu et al. |
| 2003/0228714 A1 | 12/2003 | Smith et al. |
| 2003/0229410 A1 | 12/2003 | Smith et al. |
| 2003/0229412 A1 | 12/2003 | White et al. |
| 2003/0229868 A1 | 12/2003 | White et al. |
| 2003/0229875 A1 | 12/2003 | Smith et al. |
| 2003/0229880 A1 | 12/2003 | White et al. |
| 2003/0229881 A1 | 12/2003 | White et al. |
| 2003/0237064 A1 | 12/2003 | White et al. |
| 2004/0030430 A1 | 2/2004 | Matsuoka |
| 2004/0032908 A1 | 2/2004 | Hagai et al. |
| 2004/0049722 A1 | 3/2004 | Matsushita |
| 2004/0052411 A1 | 3/2004 | Qian et al. |
| 2004/0057611 A1 | 3/2004 | Lee et al. |
| 2004/0066506 A1 | 4/2004 | Elichai et al. |
| 2004/0091142 A1 | 5/2004 | Peterson et al. |
| 2004/0094762 A1 | 5/2004 | Hess et al. |
| 2004/0098216 A1 | 5/2004 | Ye et al. |

(56) References Cited

U.S. PATENT DOCUMENTS

| | | |
|---|---|---|
| 2004/0102934 A1 | 5/2004 | Chang |
| 2004/0107412 A1 | 6/2004 | Pack et al. |
| 2004/0119036 A1 | 6/2004 | Ye et al. |
| 2004/0120569 A1 | 6/2004 | Hung et al. |
| 2004/0133369 A1 | 7/2004 | Pack et al. |
| 2004/0147121 A1 | 7/2004 | Nakagaki et al. |
| 2004/0174506 A1 | 9/2004 | Smith |
| 2004/0179738 A1 | 9/2004 | Dai et al. |
| 2004/0199885 A1 | 10/2004 | Lu et al. |
| 2004/0223639 A1 | 11/2004 | Sato et al. |
| 2004/0228515 A1 | 11/2004 | Okabe et al. |
| 2004/0234120 A1 | 11/2004 | Honda et al. |
| 2004/0243320 A1 | 12/2004 | Chang et al. |
| 2004/0246476 A1 | 12/2004 | Bevis et al. |
| 2004/0254752 A1 | 12/2004 | Wisniewski et al. |
| 2005/0004774 A1 | 1/2005 | Volk et al. |
| 2005/0008218 A1 | 1/2005 | O'Dell et al. |
| 2005/0010890 A1 | 1/2005 | Nehmadi et al. |
| 2005/0013474 A1 | 1/2005 | Sim |
| 2005/0062962 A1 | 3/2005 | Fairley et al. |
| 2005/0069217 A1 | 3/2005 | Mukherjee |
| 2005/0117796 A1 | 6/2005 | Matsui et al. |
| 2005/0132306 A1 | 6/2005 | Smith et al. |
| 2005/0141764 A1 | 6/2005 | Tohyama et al. |
| 2005/0166174 A1 | 7/2005 | Ye et al. |
| 2005/0184252 A1 | 8/2005 | Ogawa et al. |
| 2005/0190957 A1 | 9/2005 | Cai et al. |
| 2005/0198602 A1 | 9/2005 | Brankner |
| 2006/0000964 A1 | 1/2006 | Ye et al. |
| 2006/0036979 A1 | 2/2006 | Zurbrick et al. |
| 2006/0038986 A1 | 2/2006 | Honda et al. |
| 2006/0048089 A1 | 3/2006 | Schwarzband |
| 2006/0051682 A1 | 3/2006 | Hess et al. |
| 2006/0062445 A1 | 3/2006 | Verma et al. |
| 2006/0066339 A1 | 3/2006 | Rajski et al. |
| 2006/0082763 A1 | 4/2006 | Teh et al. |
| 2006/0159333 A1 | 7/2006 | Ishikawa |
| 2006/0161452 A1 | 7/2006 | Hess |
| 2006/0193506 A1 | 8/2006 | Dorphan et al. |
| 2006/0193507 A1 | 8/2006 | Sali et al. |
| 2006/0236294 A1 | 10/2006 | Saidin et al. |
| 2006/0236297 A1 | 10/2006 | Melvin, III et al. |
| 2006/0239536 A1 | 10/2006 | Shibuya et al. |
| 2006/0265145 A1 | 11/2006 | Huet et al. |
| 2006/0266243 A1 | 11/2006 | Percin et al. |
| 2006/0269120 A1 | 11/2006 | Nehmadi et al. |
| 2006/0273242 A1 | 12/2006 | Hunsche et al. |
| 2006/0273266 A1 | 12/2006 | Preil et al. |
| 2006/0277520 A1 | 12/2006 | Gennari |
| 2006/0291714 A1 | 12/2006 | Wu et al. |
| 2006/0292463 A1 | 12/2006 | Best et al. |
| 2007/0002322 A1 | 1/2007 | Borodovsky et al. |
| 2007/0011628 A1* | 1/2007 | Ouali et al. .......... 716/2 |
| 2007/0013901 A1 | 1/2007 | Kim et al. |
| 2007/0019171 A1 | 1/2007 | Smith |
| 2007/0019856 A1 | 1/2007 | Furman et al. |
| 2007/0031745 A1 | 2/2007 | Ye et al. |
| 2007/0032896 A1 | 2/2007 | Ye et al. |
| 2007/0035322 A1 | 2/2007 | Kang et al. |
| 2007/0035712 A1 | 2/2007 | Gassner et al. |
| 2007/0035728 A1 | 2/2007 | Kekare et al. |
| 2007/0052963 A1* | 3/2007 | Orbon et al. .......... 356/430 |
| 2007/0064995 A1 | 3/2007 | Oaki et al. |
| 2007/0133860 A1 | 6/2007 | Lin et al. |
| 2007/0156379 A1 | 7/2007 | Kulkarni et al. |
| 2007/0230770 A1 | 10/2007 | Kulkarni et al. |
| 2007/0248257 A1 | 10/2007 | Bruce et al. |
| 2007/0280527 A1 | 12/2007 | Almogy et al. |
| 2007/0288219 A1* | 12/2007 | Zafar et al. .......... 703/14 |
| 2008/0013083 A1 | 1/2008 | Kirk et al. |
| 2008/0049994 A1 | 2/2008 | Rognin et al. |
| 2008/0058977 A1 | 3/2008 | Honda |
| 2008/0072207 A1 | 3/2008 | Verma et al. |
| 2008/0081385 A1 | 4/2008 | Marella et al. |
| 2008/0163140 A1 | 7/2008 | Fouquet et al. |
| 2008/0167829 A1 | 7/2008 | Park et al. |
| 2008/0250384 A1 | 10/2008 | Duffy et al. |
| 2008/0295047 A1 | 11/2008 | Nehmadi et al. |
| 2008/0295048 A1 | 11/2008 | Nehmadi et al. |
| 2008/0304056 A1 | 12/2008 | Alles et al. |
| 2009/0024967 A1 | 1/2009 | Su et al. |
| 2009/0037134 A1 | 2/2009 | Kulkarni et al. |
| 2009/0041332 A1 | 2/2009 | Bhaskar et al. |
| 2009/0043527 A1 | 2/2009 | Park et al. |
| 2009/0055783 A1 | 2/2009 | Florence et al. |
| 2009/0080759 A1 | 3/2009 | Bhaskar et al. |
| 2009/0210183 A1 | 8/2009 | Rajski et al. |
| 2009/0257645 A1 | 10/2009 | Chen et al. |
| 2009/0284733 A1 | 11/2009 | Wallingford et al. |
| 2009/0290782 A1 | 11/2009 | Regensburger |
| 2010/0142800 A1 | 6/2010 | Pak et al. |
| 2010/0146338 A1 | 6/2010 | Schalick et al. |
| 2010/0150429 A1 | 6/2010 | Jau et al. |
| 2010/0226562 A1 | 9/2010 | Wu et al. |
| 2011/0052040 A1 | 3/2011 | Kuan |
| 2011/0184662 A1* | 7/2011 | Badger et al. .......... 702/35 |
| 2011/0276935 A1 | 11/2011 | Fouquet et al. |
| 2012/0308112 A1 | 12/2012 | Hu et al. |
| 2012/0319246 A1 | 12/2012 | Tan et al. |
| 2013/0009989 A1 | 1/2013 | Chen et al. |
| 2013/0027196 A1 | 1/2013 | Yankun et al. |

FOREIGN PATENT DOCUMENTS

| | | |
|---|---|---|
| CN | 1646896 | 7/2005 |
| EP | 0032197 | 7/1981 |
| EP | 0370322 | 5/1990 |
| EP | 1061358 | 12/2000 |
| EP | 1061571 | 12/2000 |
| EP | 1065567 | 1/2001 |
| EP | 1066925 | 1/2001 |
| EP | 1069609 | 1/2001 |
| EP | 1093017 | 4/2001 |
| EP | 1329771 | 7/2003 |
| EP | 1480034 | 11/2004 |
| EP | 1696270 | 8/2006 |
| JP | 7-159337 | 6/1995 |
| JP | 2002-071575 | 3/2002 |
| JP | 2002-365235 | 12/2002 |
| JP | 2003-215060 | 7/2003 |
| JP | 2004-045066 | 2/2004 |
| JP | 2005-283326 | 10/2005 |
| JP | 2009-122046 | 6/2009 |
| KR | 10-2001-0007394 | 1/2001 |
| KR | 10-2001-0037026 | 5/2001 |
| KR | 10-2001-0101697 | 11/2001 |
| KR | 10-2003-0055848 | 7/2003 |
| KR | 10-2006-0075691 | 7/2005 |
| KR | 10-2005-0092053 | 9/2005 |
| KR | 10-2010-0061018 | 6/2010 |
| WO | 98/57358 | 12/1998 |
| WO | 99/22310 | 5/1999 |
| WO | 99/25004 | 5/1999 |
| WO | 99/59200 | 5/1999 |
| WO | 99/38002 | 7/1999 |
| WO | 99/41434 | 8/1999 |
| WO | 00/03234 | 1/2000 |
| WO | 00/36525 | 6/2000 |
| WO | 00/55799 | 9/2000 |
| WO | 00/68884 | 11/2000 |
| WO | 00/70332 | 11/2000 |
| WO | 01/09566 | 2/2001 |
| WO | 01/40145 | 6/2001 |
| WO | 03/104921 | 12/2003 |
| WO | 2004/027684 | 4/2004 |
| WO | 2006/012388 | 2/2006 |
| WO | 2006/063268 | 6/2006 |
| WO | 2009/152046 | 9/2009 |
| WO | 2010/093733 | 8/2010 |

OTHER PUBLICATIONS

U.S. Appl. No. 60/684,360, filed May 24, 2005 by Nehmadi et al.
U.S. Appl. No. 13/652,377, filed Oct. 15, 2012 by Wu et al.

(56) References Cited

OTHER PUBLICATIONS

Allan et al., "Critical Area Extraction for Soft Fault Estimation," IEEE Transactions on Semiconductor Manufacturing, vol. 11, No. 1, Feb. 1998.

Barty et al., "Aerial Image Microscopes for the inspection of defects in EUV masks," Proceedings of SPIE, vol. 4889, 2002, pp. 1073-1084.

Budd et al., "A New Mask Evaluation Tool, the Microlithography Simulation Microscope Aerial Image Measurement System," SPIE vol. 2197, 1994, pp. 530-540.

Cai et al., "Enhanced Dispositioning of Reticle Defects Using the Virtual Stepper With Automoated Defect Severity Scoring," Proceedings of the SPIE, vol. 4409, Jan. 2001, pp. 467-478.

Diebold et al., "Characterization and production metrology of thin transistor gate oxide films," Materials Science in Semiconductor Processing 2, 1999, pp. 103-147.

Dirksen et al., "Impact of high order aberrations on the performance of the aberration monitor," Proc. Of SPIE vol. 4000, Mar. 2000, pp. 9-17.

Dirksen et al., "Novel aberration monitor for optical lithography," Proc. Of SPIE vol. 3679, Jul. 1999, pp. 77-86.

Garcia et al., "New Die to Database Inspection Algorithm for Inspection of 90-nm Node Reticles," Proceedings of SPIE, vol. 5130, 2003, pp. 364-374.

Granik et al- "Sub-resolution process windows and yield estimation technique based on detailed full-chip CD simulation," Mentor Graphics, Sep. 2000, 5 pages.

Hess et al., "A Novel Approach: High Resolution Inspection with Wafer Plane Defect Detection," Proceedings of SPIE—International Society for Optical Engineering; Photomask and Next-Generation Lithography Mask Technology 2008, vol. 7028, 2008.

Huang et al., "Process Window Impact of Progressive Mask Defects, Its Inspection and Disposition Techniques (go/no-go criteria) Via a Lithographic Detector," Proceedings of SPIE—The International Society for Optical Engineering; 25th Annual Bacus Symposium on Photomask Technology 2005, vol. 5992, No. 1, 2005, p. 6.

Huang et al., "Using Design Based Binning to Improve Defect Excursion Control for 45nm Production," IEEE, International Symposium on Semiconductor Manufacturing, Oct. 2007, pp. 1-3.

Karklin et al., "Automatic Defect Severity Scoring for 193 nm Reticle Defect Inspection," Proceedings of SPIE—The International Society for Optical Engineering, 2001, vol. 4346, No. 2, pp. 898-906.

Lo et al., "Identifying Process Window Marginalities of Reticle Designs for 0.15/0.13 μm Technologies," Proceedings of SPIE vol. 5130, 2003, pp. 829-837.

Lorusso et al. "Advanced DFM Appins. Using design-based metrology on CDSEM," SPIE vol. 6152, Mar. 27, 2006.

Lu et al., "Application of Simulation Based Defect Printability Analysis for Mask Qualification Control," Proceedings of SPIE, vol. 5038, 2003, pp. 33-40.

Mack, "Lithographic Simulation: A Review," Proceedings of SPIE vol. 4440, 2001, pp. 59-72.

Martino et al., "Application of the Aerial Image Measurement System (Aims(TM)) to the Analysis of Binary Mask Imaging and Resolution Enhancement Techniques," SPIE vol. 2197, 1994, pp. 573-584.

Nagpal et al., "Wafer Plane Inspection for Advanced Reticle Defects," Proceedings of SPIE—The International Society for Optical Engineering; Photomask and Next-Generation Lithography Mask Technology. vol. 7028, 2008.

Numerical Recipes in C. The Art of Scientific Computing, 2nd Ed., @ Cambridge University Press 1988, 1992, p. 683.

O'Gorman et al., "Subpixel Registration Using a Concentric Ring Fiducial," Proceedings of the International Conference on Pattern Recognition, vol. ii, Jun. 16, 1990, pp. 249-253.

Otsu, "A Threshold Selection Method from Gray-Level Histograms," IEEE Transactions on Systems, Man, and Cybernetics, vol. SMC-9, No. 1, Jan. 1979, pp. 62-66.

Pang et al., "Simulation-based Defect Printability Analysis on Alternating Phase Shifting Masks for 193 nm Lithography," Proceedings of SPIE, vol. 4889, 2002, pp. 947-954.

Pettibone et al., "Wafer Printability Simulation Accuracy Based on UV Optical Inspection Images of Reticle Defects," Proceedings of SPIE—The International Society for Optical Engineering 1999 Society of Photo-Optical Instrumentation Engineers, vol. 3677, No. II, 1999, pp. 711-720.

Phan et al., "Comparison of Binary Mask Defect Printability Analysis Using Virtual Stepper System and Aerial Image Microscope System," Proceedings of SPIE—The International Society for Optical Engineering 1999 Society of Photo-Optical Instrumentation Engineers, vol. 3873, 1999, pp. 681-692.

Sahouria et al., "Full-chip Process Simulation for Silicon DRC," Mentor Graphics, Mar. 2000, 6 pages.

Sato et al., "Defect Criticality Index (DCI): A new methodology to significantly improve DOI sampling rate in a 45nm production environment," Metrology, Inspection, and Process Control for Microlithography XXII, Proc. Of SPIE vol. 6922, 692213 (2008), pp. 1-9.

Schurz et al., "Simulation Study of Reticle Enhancement Technology Applications for 157 nm Lithography," SPIE vol. 4562, 2002, pp. 902-913.

Svidenko et al. "Dynamic Defect-Limited Yield Prediction by Criticality Factor," ISSM Paper: YE-O-157, 2007.

Tang et al., "Analyzing Volume Diagnosis Results with Statistical Learning for Yield Improvement" 12th IEEE European Test Symposium, Freiburg 2007, IEEE European, May 20-24, 2007, pp. 145-150.

Volk et al. "Investigation of Reticle Defect Formation at DUV Lithography," 2002, BACUS Symposium on Photomask Technology.

Volk et al. "Investigation of Reticle Defect Formation at DUV Lithography," 2003, IEEE/SEMI Advanced Manufacturing Conference, pp. 29-35.

Volk et al., "Investigation of Smart Inspection of Critical Layer Reticles using Additional Designer Data to Determine Defect Significance," Proceedings of SPIE vol. 5256, 2003, pp. 489-499.

Yan et al., "Printability of Pellicle Defects in DUV 0.5 um Lithography," SPIE vol. 1604, 1991, pp. 106-117.

Guo et al., "License Plate Localization and Character Segmentation with Feedback Self-Learning and Hybrid Binarization Techniques," IEEE Transactions on Vehicular Technology, vol. 57, No. 3, May 2008, pp. 1417-1424.

Liu, "Robust Image Segmentation Using Local Median," Proceedings of the 3rd Canadian Conference on Computer and Robot Vision (CRV'06) 0-7695-2542-3/06, 2006 IEEE, 7 pages total.

* cited by examiner

ALTERATION FOR WAFER INSPECTION

BACKGROUND OF THE INVENTION

1. Field of the Invention

This invention generally relates to methods and systems for design alteration for wafer inspection.

2. Description of the Related Art

The following description and examples are not admitted to be prior art by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices. However, as the dimensions of semiconductor devices decrease, inspection becomes even more important to the successful manufacture of acceptable semiconductor devices because smaller defects can cause the devices to fail.

Every fab is interested in detecting defects that are relevant to yield. To achieve this, defect engineers utilize various approaches in defining knowledge-based inspection care area and binning approaches. As such, design-based inspection and binning have been widely adopted by advanced fabs in the semiconductor industry. However, despite these efforts, defect data is still convoluted with nuisance defect data, which impacts defect binning, resulting in many nuisance bins among the pattern groups.

Existing methods for removing nuisance defects involve much effort in recipe setup and post-processing. In setup, smaller care areas (CAs) may be defined based on user knowledge and building of a defect organizer such as iDO, which is commercially available from KLA-Tencor, Milpitas, Calif. In post-processing, various inspection attributes such as energy and contrast or design-based binning methods are used to filter out nuisance defects. Although some filtering may be applied to defect detection results prior to binning, significant numbers of nuisance defects are included in the defect detection results used for binning. In the case of design-based binning, binning can lead to thousands of groups since all patterns (whether critical or not) are used to generate pattern groups. Such a huge number of defect groups creates a significant challenge in identifying critical pattern types among relatively large numbers of groups. For example, the number of groups may be substantially high and contain a substantially large number of nuisance bins, making it difficult to isolate important pattern groups. While design-based binning provides significant advantages over other types of defect binning methods, such binning introduces additional challenges and time to process data upon inspection. There is also no easy way to remove the nuisance bins, and computing resources used to bin defects into the nuisance groups are essentially wasted and reduce productivity.

Accordingly, it would be advantageous to develop systems and/or methods that do not have one or more of the disadvantages described above.

SUMMARY OF THE INVENTION

The following description of various embodiments is not to be construed in any way as limiting the subject matter of the appended claims.

One embodiment relates to a computer-implemented method for binning defects on a wafer. The method includes identifying areas in a design for a layer of a device being fabricated on a wafer that are not critical to yield of fabrication of the device. The method also includes generating an altered design for the layer by eliminating features in the identified areas from the design for the layer. In addition, the method includes detecting defects on the layer using output of an inspection system. The method further includes binning the defects into groups using the altered design such that features in the altered design proximate positions of the defects in each of the groups are at least similar. The identifying, generating, detecting, and binning steps are performed by one or more computer systems.

The method described above may be performed as described further herein. In addition, the method described above may include any other step(s) of any other method(s) described herein. Furthermore, the method described above may be performed by any of the systems described herein.

Another embodiment relates to a non-transitory computer-readable medium storing program instructions executable on a computer system for performing a computer-implemented method for binning defects on a wafer. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

An additional embodiment relates to a system configured to bin defects on a wafer. The system includes an inspection system configured to generate output for a layer in a device being fabricated on a wafer. The system also includes one or more computer systems configured for performing the steps of the method described above. The system may be further configured as described herein.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a computer-implemented method for binning defects on a wafer. As will be described further herein, the embodiments may include rule-based yield-sensitive design layout generation for separation of critical and non-critical areas in a design.

The method includes identifying areas in a design for a layer of a device being fabricated on a wafer that are not critical to yield of fabrication of the device. Therefore, the identifying step may include identifying critical and non-critical areas in the design. By separating critical areas from non-critical areas as described herein, the identifying step effectively identifies patterns of interest (POIs) or the patterns of features located in areas that are critical to the yield. Although the embodiments will be described herein with respect to a layer of a device, the method may be performed for any one or more layers or all layers of the device separately. For example, the method may be performed for the metal 1 (M1) layer of a device, and the method may be performed for the metal 2 (M2) layer of the device.

In one embodiment, identifying the areas is performed using a design layout file for the design. The design layout file may be a Graphical Data System (GDS) or Open Artwork System Interchange Standard (OASIS) file. The design or design layout file used in the embodiments described herein may include any other design layout file known in the art. In addition, the design layout file used in the identifying step may have any configuration such as for a cut mask, double patterning lithography (DPL), composite layers, self-aligned double patterning (SADP), etc. The method may include acquiring the design layout file from an electronic design automation (FDA) tool. The design layout file can be preprocessed to identify areas that are prone to yield loss due to defects as described further herein.

In some embodiments, identifying the areas includes identifying the areas in the design for the layer that are not critical to the yield by applying user-defined rules to a design layout file for the design. In this manner, identifying the areas may include rule-based identification, and the methods may include using user-defined rules to identify critical areas. The user-defined rules may be based on any one or more characteristics of the features in the design such as the characteristics described herein (e.g., density of features, dimensions of spaces between features, etc.). The user-defined rules may be acquired in any suitable manner. For example, the method may be configured to acquire the user-defined rules from a storage medium. Alternatively, the method may include displaying a user interface to the user (e.g., using one of the computer systems described further herein) and receiving the user-defined rules from the user through the user interface.

In another embodiment, identifying the areas includes identifying the areas in the design for the layer that are not critical to the yield based on density of the features in different areas in the design for the layer. For example, in reality, relatively small defects or pattern abnormalities in relatively sparse regions of a die have minimal or no impact on yield. In contrast, defects of any size in relatively dense areas of the design can have significant impacts on the yield. The density of the features that separates sparse and therefore not critical areas from dense and therefore critical areas may be set in any suitable manner.

In one embodiment, identifying the areas includes identifying the areas in the design for the layer that are not critical to the yield based on dimensions of spaces between the features in different areas of the design for the layer. For example, defects falling in minimal feature areas (minimal spaces almost always have significant impact on yield. In other words, defects landing in minimal spaces will generally be critical defects. In one example, a 50 nm pattern defect located in a 200 nm space will not likely cause yield loss where the same defect located in a 50 nm space will likely short out the lines or other features located on either side of the space. Areas with minimum spaces can be identified by using the design for the layer to determine the minimum dimension of spaces in the design. The absolute minimum dimension of all of the spaces in the design can be used to determine some range of dimensions for spaces that can be considered minimal and to thereby generate a threshold for identifying areas having "minimum spaces" and those that do not. For example, the absolute minimum can be increased by a percentage, say 10%, or by an absolute value and that "increased minimum" may be used as a threshold for separating areas in the design into those that are critical to yield and those that are not.

In some embodiments, identifying the areas includes identifying the areas in the design for the layer that are not critical to the yield based on dimensions of the features in different areas of the design for the layer. For example, defects falling in areas having minimal feature dimensions (minimal line widths or minimal areas of features) almost always have significant impact on yield. A threshold that can be used to separate areas based on dimensions of the features may be determined by determining the minimum feature dimension in the design for the layer and setting the threshold value based on the minimum feature dimension. For example, the threshold may be equal to the minimum feature dimension, the minimum feature dimension increased by some percentage or absolute value, etc. Areas that include only features whose minimum dimensions are greater than that threshold may be identified as not critical to the yield. Any other areas may be identified as critical to the yield.

In an additional embodiment, identifying the areas includes identifying the areas in the design for the layer that are not critical to the yield based on function of the features in the different areas of the design for the layer. For example, areas of the design that include only supporting structures, dummy features, or features used as fillers may be identified as areas that are not critical to the yield. Therefore, main layer features can be separated from supporting structures and dummy patterns. The function of the features can be determined directly from the design for the layer in any suitable manner.

Identifying the areas that are not critical to the yield may be performed in only one manner described above or in more than one manner described above. For example, if an area includes only features whose minimum dimensions are less than the threshold for feature dimension, that area will generally not include dummy features or supporting structures and therefore examining the function of those features will generally not be beneficial. However, identifying the areas may include evaluating a number of characteristics of the design simultaneously or sequentially. For example, areas of the design that only include supporting structures or dummy features may be identified and therefore eliminated to generate one altered design and then this altered design may be evaluated for minimum space dimensions and any areas that do not include spaces having a minimum dimension below some threshold may be eliminated from that altered design to generate another altered design. The second altered design may be further processed or used in other steps described herein such as binning.

Figure 1:
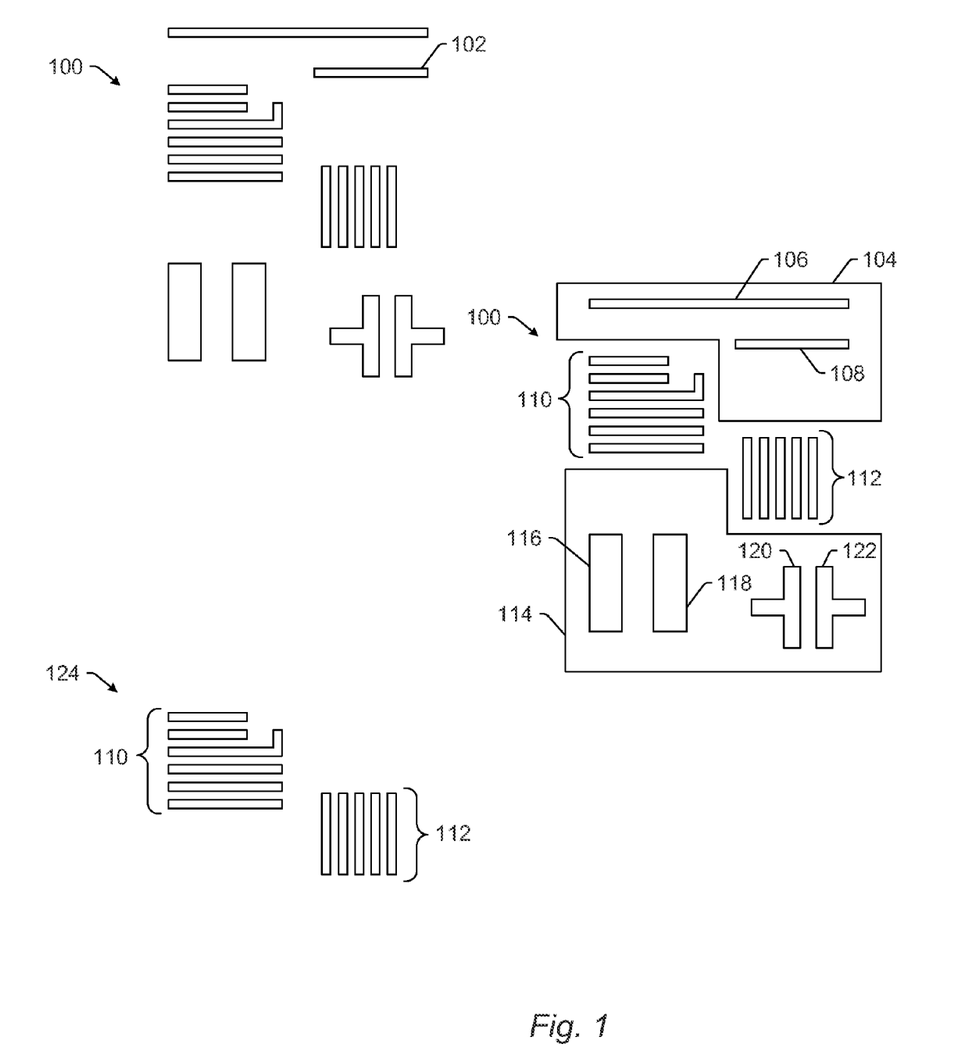
FIG. 1 is a schematic diagram illustrating one example of a design and one embodiment of an altered design that may be generated for the design by the embodiments described herein.

FIG. 1 illustrates an example of a portion of a design for a hypothetical layer of a wafer and various results of the identifying steps described above. For example, as shown in FIG. 1, a portion of design 100 may include a number of different features 102. As shown in FIG. 1, the different features may include features that have different shapes, different orientations (e.g., horizontal and vertical), and different dimensions. In addition, the portion of the design shown includes areas that have different densities of features.

Area 104 in design 100 that includes features 106 and 108 may be identified as an area of the design that is not critical to yield of the device fabrication in a number of different manners described herein. For example, features 106 and 108 may have a width that is equal to the minimum line width of all the features in the design, but since the space between the features included in area 104 is substantially larger than the line width dimension of the features, the area does not include spaces having minimum dimensions. Therefore, the area containing features 106 and 108 may be identified as an area that is not critical to yield.

Area 104 may also be identified in other manners described herein. For example, not only are the features in area 104 separated by a space having a dimension substantially greater than the minimum dimension, the features in this area are relatively sparse due to the dimensions of the space between them. Therefore, if the identifying step was performed based on density as described above, this area would also be identified as not critical to yield of the device fabrication. As such, area 104 may be identified in a number of different manners described herein, but once the area is identified in one manner, that area may be identified as not critical to yield and not evaluated further if identifying the areas is performed in any other manner.

Area 114 in design 100 that includes features 116, 118, 120 and 122 may also be identified as an area of the design that is not critical to yield of the device fabrication in a number of different manners described herein. For example, features 116 and 118 included in area 114 are separated by a space having a dimension that is equal to the smallest dimension of the features, and features 120 and 122 are separated from each other by a space having a dimension that is equal to the smallest dimension of those features, but since the smallest dimensions of features 116, 118, 120 and 122 are substantially greater than the minimum feature dimension in the design, features 116, 118, 120 and 122 will not have minimum spaces between them and will not have minimum feature dimensions. Therefore, the area containing features 116, 118, 120 and 122 may be identified as an area that is not critical to yield.

Area 114 may also be identified in other manners described herein. For example, since the features in area 114 are separated by spaces having dimensions greater than the minimum space in the design and have feature dimensions that are greater than the minimum feature dimension in the design, the features in this area may be relatively sparse due to the dimensions of the features and the spaces between them. Therefore, if the identifying step was performed as described above based on density, this area would also be identified as not critical to yield of the device fabrication. As such, area 114 may be identified in a number of different manners described herein, but once the area is identified in one manner, that area may be identified as not critical to yield and not evaluated further if identifying the areas is performed in any other manner.

Any other characteristics of a device design relevant to yield of device fabrication may also be taken into consideration when identifying the areas that are not critical to yield. For example, identifying the areas may include using information about array edges in the design to determine if features in an area of the design are critical to yield, which may in of itself be used to identify the areas or may be used in combination with other manners for identification described above. In addition, information about other layers of the design (a layer to be formed on the wafer subsequent to the layer in question (i.e., a future layer) or a layer that is or will be formed on the wafer prior to the layer in question (i.e., a previous layer)) may be used in combination with the design for the layer to determine areas of the layer that are not critical to yield. For example, if an area of the design for the layer is determined to be not critical to the layer in a manner described herein but is located above or below a critical area of the design for a future or previous layer of the device, that area may be identified as critical where, taking into consideration only the layer itself, it would have been identified as not critical. Furthermore, pattern searching may be used to identify areas that are not critical to yield. For example, if a particular pattern is known a priori to be critical or not critical to yield, the design may be searched for those patterns using any suitable pattern matching method and/or algorithm and the areas containing them may be identified accordingly. In addition, design rule checking (DRC) information or software may be used for identifying areas that are not critical to the yield.

The method also includes generating an altered design for the layer by eliminating features in the identified areas from the design for the layer. The features in the altered design may include features in areas of the design for the layer other than the identified areas. For example, with the knowledge gained in the identifying step described above, design layout files can be pre-processed in the generating step to eliminate or group the identified areas before sending the design to the binning operation. In one such example, a new layout can be created for only the areas that have a minimum space. In this manner, non-critical patterns can be eliminated from the design. Since the identified areas that are eliminated include areas that are not critical to the yield, eliminating features in those identified areas produces a yield-sensitive design layout by separating critical and non-critical areas of the design. Therefore, the altered design may also be referred to as a "yield critical layout" in that it includes only those device features that are critical to the yield of device fabrication.

In the example shown in FIG. 1, generating an altered design may include eliminating features 106, 108, 116, 118, 120, and 122 in identified areas 104 and 114 from the design for the layer. Altered design 124 will then include features 110 and 112 in areas of the design other than the identified areas 104 and 114. In this manner, areas of the design other than the identified areas are new areas that can be created for critical areas. Therefore, features 110 and 112 and any other features not eliminated in the generating step will be included in the altered design. As such, a new layout can be created by feature elimination.

Using the altered design in additional steps described herein provides a number of advantages. For example, any defects that are detected in the identified areas will most likely be nuisance defects or defects that the user does not care about because those defects will be located in areas that are not critical to yield. Therefore, those areas and the features located therein can be considered as a nuisance source and eliminating them from the design eliminates a nuisance source from the design. As such, the embodiments described herein are advantageous since a nuisance source can be eliminated from the design and therefore before inspection or any steps are performed with the altered design thereby reducing the computation requirement for the inspection system or any other system that uses the altered design instead of the design. For example, areas that are not critical can be eliminated from the design layout and this customized layout can be used for defect binning such as that described further herein. In addition to reducing the computation requirement of steps performed using the altered design instead of the original design, the embodiments described herein reduce the data size used in such steps for easier data handling.

In one embodiment, generating the altered design includes eliminating the features in the identified areas from a design layout file for the design thereby creating a modified design layout file and converting a file format of the modified design layout file to a different file format that can be used for the binning step described further herein. In this manner, the non-critical patterns in the design layout can be eliminated prior to creating a design layout for use by an inspection system or method. Therefore, one advantage of the embodiments described herein is that any intellectual property in the original design can be protected since the modified design layout file contains insufficient data to build a device. As such, the embodiments can reduce any intellectual property concerns by fragmenting the design file. In addition, by converting the altered design (or modified design layout) to another format, the modified layout file generated as described herein may be non-functional and have a format that is specific for inspection. The file format of the modified design layout file can be converted in any suitable manner into any file format such as those that can be used by commercially available inspection systems.

Generating the altered design may also include eliminating the features in the identified areas and replacing features in areas of the design for the layer other than the identified areas with different features. For example, the features in the identified areas may be eliminated as described above. Then, the design layout that includes the remaining features may be changed from its original intent to something totally different that can be used for inspection and binning purposes. For example, the altered design can be generated by adding and subtracting features to create new features that are not present in the original design layout and to create new design layout that does not show the original design intent.

In one such example shown in FIG. 1, the altered design may be generated as described above by eliminating the features in the identified areas resulting in features 110 and 112 remaining in altered design 124. Generating the altered design may then include generating spaces around the remaining features. For example, space 126 may be generated around features 110 and space 128 may be generated around features 112. In this manner, creating the new design layout may include adding spaces to the original design or the altered design from which features in noncritical areas have been eliminated.

Generating the altered design may then include adding and subtracting any areas in the spaces that do not include features or portions of the features having one or more characteristics such as those described above. For example, as shown in FIG. 1, space 126 may be reduced to space 130 that results in a portion of one of features 110 being located outside of space 130. The portion of the feature may be eliminated from space 130 since it is spaced from other features 110 by more than a minimum dimension. Therefore, the portion of the feature eliminated from space 130 may be non-critical to the yield of the device and may be eliminated from the altered design as described herein. However, as shown in FIG. 1, since each of the spaces between adjacent features 112 have a minimum dimension for the spaces, space 128 and space 132 may be the same since no portion of the features within space 128 can be eliminated as non-critical.

Generating the altered layout may then include subtracting the remaining features in spaces 130 and 132 from those spaces to create new features in a new design layout. For example, subtracting features 110 from space 130 results in features 136 that include a number of spaces 134. In addition, subtracting features 112 from space 132 results in features 140 that include a number of spaces 138. Therefore, only the empty spaces that remain after the steps described above may be used to generate the new design layout.

The altered design does not include care areas. In addition, the method does not include generating care areas for the design, the altered design, or the wafer. For example, some currently used methods and systems use the layout file to create care areas for inspection, but this is not to be confused with the embodiments described herein. In particular, the embodiments described herein do not create care areas but use the design layout to identify critical areas. In addition, unlike care area generation methods and systems, the altered design generated by the embodiments described herein may retain the features in the areas identified as critical to yield. In contrast, generating care areas generally involves determining characteristics of the care areas such as dimensions and coordinates, but the care areas themselves and the characteristics of the care areas do not include any features in the design.

In another embodiment, the altered design does not include information for criticality of the areas in the design for the layer. For example, since the altered design does not include features in the design that are not critical to the yield, the altered design may only include features in the design that are critical to yield. Therefore, information about the yield criticality of different features in the design can be determined based on the presence or absence of features in the altered design, but the altered design itself does not include any information about criticality such as tags or other indicia indicating which areas are critical and which are not.

The method also includes detecting defects on the layer using output of an inspection system. The output of the inspection system may include any output generated by any inspection system such as that described further herein. For example, the output may include signals or data generated by one or more detectors of the inspection system. The method may include acquiring the output of the inspection system by using the inspection system to scan the wafer and generating output responsive to light from the wafer during the scanning. Alternatively, the method may include acquiring the output from a storage medium in which the output has been stored (e.g., by the inspection system). Detecting the defects using the output may be performed using any suitable defect detection method and/or algorithm known in the art. For example, detecting the defects may include subtracting the output generated at a within die position in a reference die from the output generated at the same within die position in a test die and comparing the subtraction results to a threshold. Any subtraction results above the threshold may be identified as defects or possible defects.

In one embodiment, detecting the defects is performed without regard to position of the output of the inspection system with respect to the altered design. For example, all of the output that is generated by the inspection system may be used for defect detection that is performed with the highest sensitivity available on the inspection system. The highest available sensitivity is often not used for inspection or for inspection performed using all of the output generated for a wafer because of the substantially high numbers of defects that will be detected on the wafer with that sensitivity, which increases the complexity and decreases the throughput of any functions performed on the inspection results. However, as will be described further herein, binning may be performed such that any defects that are not located on, near, or proximate to features in the altered design may not be binned into any groups and may thereby be eliminated from any functions performed using the binning results. In other words, the binning may effectively eliminate defects in non-critical areas of the design from the inspection results thereby eliminating the deleterious effect that large numbers of nuisance defects can have on steps performed using the inspection results. In addition, unlike some methods that select the defect detection to be performed based on position of the output with respect to the design or position of the output in design data space, since additional steps described herein will be performed using the altered design that includes only features in areas that are yield critical, the same defect detection can be performed for all areas in the design.

The method also includes binning the defects into groups using the altered design such that features in the altered design proximate positions of the defects in each of the groups are at least similar. In this manner, the binning step may include using the modified layout file to group defects according to critical pattern. For example, the position of a defect may be determined with respect to the altered design in any suitable manner (e.g., by aligning the altered design to the output of the inspection system for the wafer). The features in the altered design that are at or proximate to the position of the defect with respect to the altered design may then be determined. Features that are "at" the position of the defect with respect to the altered design may be defined as features on which the defect is completely or partially located. In this manner, the location of features "at" the position of a defect and the location of the defect may completely or partially overlap. Features in the altered design that are "proximate to" a position of a defect with respect to the altered design may be defined as features that are immediately adjacent to a defect (i.e., next to a defect) or features that are spaced from a defect but are still "near" the defect features and defects that are spaced apart by a dimension equal to or less than a critical dimension of the design for the layer or some dimension defined by the user). Therefore, features that are "proximate to" a position of a defect with respect to the altered design would include features that are "at" the position of the defect.

If any features are located at or proximate to the position of the defect, those features may be compared to the features at or proximate the positions of other defects. Determining if the features in the altered design are at least similar may include comparing results of the feature comparing step with predetermined criteria for similarity. For example, results of the comparing step may be compared to a threshold value. If the features in the altered design are at least similar by at least this threshold value, the method may bin the defects in a group. In this manner, detects located proximate to similar features may be binned into the same group. In another example, results of the comparing step may be compared to a "percent similar" value. If the features in the altered design are at least similar by at least this percent, then the method may bin the defects in a group.

Binning the defects as described above may also be performed in any other manner described in U.S. Pat. No. 7,570, 796 issued on Aug. 4, 2009 to Zafar et al., which is incorporated by reference as if fully set forth herein. In addition, binning the defects as described above may be performed using any commercially available design-based binning methods by substituting the altered design generated as described herein for any design used by those binning methods. Therefore, the embodiments described herein can be implemented immediately by leveraging existing design-based binning technology. Since only yield critical areas are fed into the binning step (by eliminating unwanted polygons from the design as described further herein), the computation load or requirement of the binning step is reduced and throughput is faster.

One of the main challenges today for the inspection industry is to remove nuisance from inspection data. By removing non-critical areas from the design layout data as described herein, an altered design can be created that can be used to reduce nuisance while grouping defects that are only in critical areas in a device layout. For example, in one embodiment, in the binning step, the defects having positions that are not proximate any of the features in the altered design are not binned into any of the groups. Since features located in areas that are not critical to the yield have been eliminated from the design, defects that are not relevant to yield will not be binned into any groups since any features to which these defects may be proximate will have been eliminated from the design. In this manner, defects that are not relevant to the yield can be automatically separated from other defects by the binning step. In other words, using the yield-aware design layout (i.e., the altered layout) for grouping of defect data, defects can be separated into critical defects and nuisance defects automatically.

In this manner, the embodiments described herein reduce the nuisance defects in binning results such as pareto charts. For example, the number of defect groups included in binning results such as pareto charts can be drastically reduced in the embodiments described herein compared to other binning methods. Therefore, the binning results will include less nuisance. In addition, reducing the number of bins, and in particular the number of nuisance bins, can lead to improved defect sampling for other steps performed using the inspection results such as defect review. In other words, grouping defects by critical pattern only can lead to better review sampling (e.g., for DOI identification or for a better chance of sampling DOI for defect review). Nuisance defect reduction by separating critical from non-critical areas as described herein can also lead to better POI identification (e.g., where POI identification involves identifying patterns located in critical areas that are prone to defects).

In another embodiment, information about which of the areas in the layer are not critical to the yield is not used for the detecting and binning steps. For example, since the altered design does not include features in the design that are not critical to the yield, the altered design may only include features in the design that are critical to yield. Therefore, information about the yield criticality of different features in the design may be determined based on the presence or absence of features in the altered design, but the altered design itself does not include any information about criticality such as tags or other indicia indicating which areas are critical and which are not. Therefore, although the binning step described herein is performed using the altered design from which features in non-critical areas have been eliminated, the binning step is not performed based on information about which of the areas in the layer are critical to the yield and which are not. In a similar manner, detecting the defects as described above may be performed without regard to which areas in the layer are critical to the yield and which are not. For example, as described further above, the same detect detection method and/or algorithm with the same defect detection parameters such as threshold may be used to detect defects in all areas of the design regardless of the yield criticality of the different areas.

Identifying the areas, generating the altered design, detecting the defects, and binning the defects are performed by one or more computer systems, which may be configured as described further herein.

In one embodiment, the one or more computer systems that perform the identifying and generating steps include a computer system of an EDA tool. For example, an EDA tool may be used to determine yield critical areas in a design layout file. In addition, the embodiments may be implemented by using currently available EDA tools (or design rule checking (DRC) software) by tailoring the EDA tool function for the embodiments described herein thereby taking advantage of existing data plumbing while using the EDA tool in a new manner. In particular, without building new infrastructure, EDA tool capability can be tailored for the embodiments described herein. The one or more computer systems that are used to perform the identifying and generating steps and the EDA tool may be further configured as described herein.

In another embodiment, the one or more computer systems that perform the detecting and binning steps include a computer system of the inspection system. The computer system of the inspection system may be further configured as described herein. Therefore, different computer systems may be used to perform different steps of the method. As described further herein, the different computer systems may be configured such that the altered design generated by one computer system can be sent to and received by another computer system that performs one or more steps such as binning using the altered design. Although using different computer systems to perform different steps of the method may be advantageous, one computer system can be used to perform all steps of the methods described herein. For example, in some instances, a stand alone computer system or a virtual inspector (VI) such as that described in U.S. Pat. No. 8,126,255 issued on Feb. 28, 2012 to Bhaskar et al., which is incorporated by reference as if fully set forth herein, may be used to perform all steps of the methods described herein.

In some embodiments, the inspection system is a light-based inspection system. In this manner, the inspection tool may be an optical inspection tool. In some embodiments, the inspection system is an electron beam-based inspection system. The inspection system may include any suitable commercially available light- or electron beam-based inspection system known in the art. In addition, the light-based inspection system may be a bright field (BF) and/or dark field (DF) inspection system. In this manner, the inspection system used in the embodiments described herein is not limited to BF, DF, and/or electron beam inspection. In other words, the embodiments described herein are independent of the inspection system platform.

Each of the embodiments of the method described above may include any other step(s) of any other method(s) described herein. Furthermore, each of the embodiments of the method described above may be performed by any of the systems described herein.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc.

Figures 2, 3:
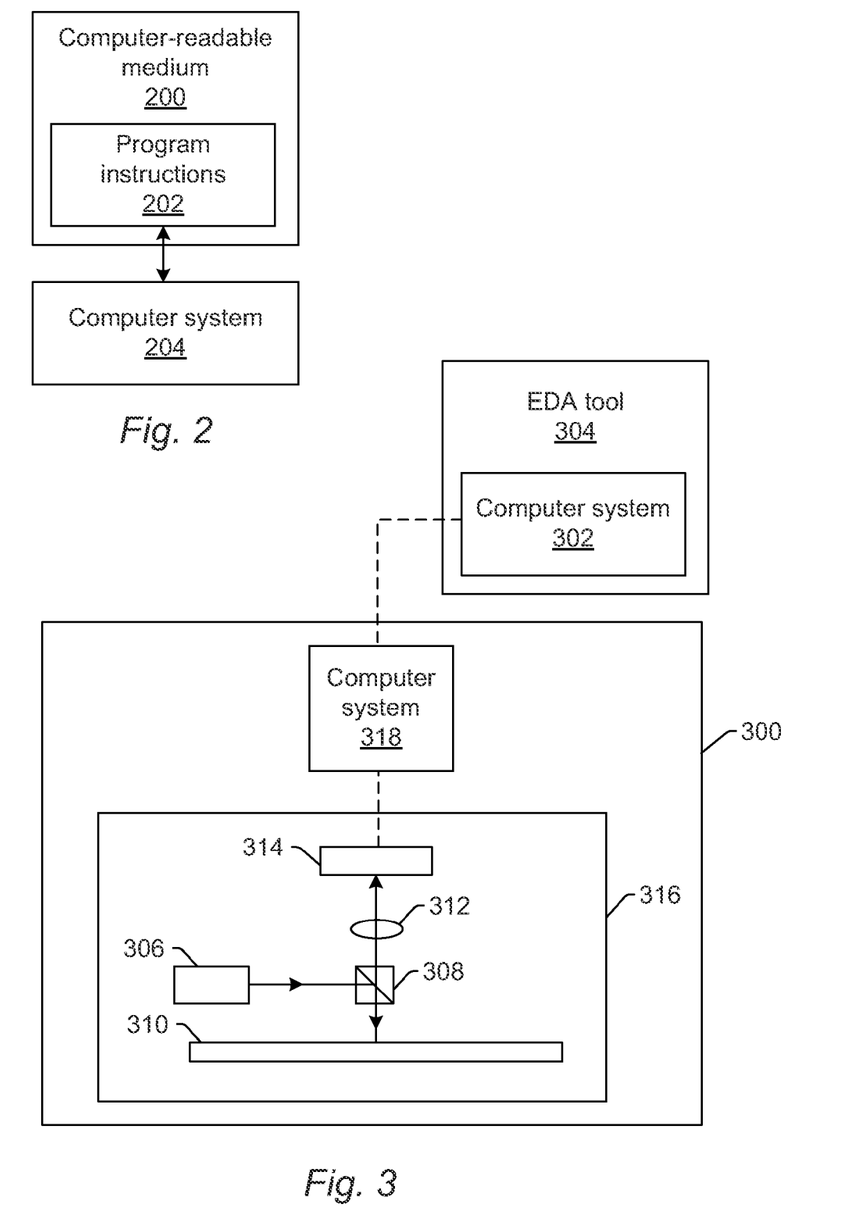
FIG. 2 is a block diagram illustrating one embodiment of a non-transitory computer-readable medium that includes program instructions executable on a computer system for performing one or more of the computer-implemented methods described herein.
FIG. 3 is a schematic diagram illustrating a side view of one embodiment of a system configured to bin defects on a wafer.

An additional embodiment relates to a non-transitory computer-readable medium storing program instructions executable on a computer system for performing a computer-implemented method for binning defects on a wafer. One such embodiment is shown in FIG. 2. In particular, as shown in FIG. 2, computer-readable medium 200 includes program instructions 202 executable on computer system 204. The computer-implemented method includes the steps of the method described above. The computer-implemented method for which the program instructions are executable may include any other step(s) described herein.

Program instructions 202 implementing methods such as those described herein may be stored on computer-readable medium 200. The computer-readable medium may be a storage medium such as a magnetic or optical disk, or a magnetic tape or any other suitable non-transitory computer-readable medium known in the art.

The program instructions may be implemented in any of various ways, including procedure-based techniques, component-based techniques, and/or object-oriented. techniques, among others. For example, the program instructions may be implemented using ActiveX controls, C++ objects, Java-Beans, Microsoft Foundation Classes ("MFC"), or other technologies or methodologies, as desired.

The computer system may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer system may also include any suitable processor known in the art such as a parallel processor. In addition, the computer system may include a computer platform with high speed processing and software, either as a standalone or a networked tool.

An additional embodiment relates to a system configured to bin defects on a wafer. One embodiment of such a system is shown in FIG. 3. The system includes inspection system 300 configured to generate output for a layer in a device being fabricated on a wafer, which is configured in this embodiment as described further herein. The system also includes one or more computer systems configured for performing the identifying, generating, detecting, and binning steps described herein. The one or more computer systems may be configured to perform these steps according to any of the embodiments described herein. The computer system(s) and the system may be configured to perform any other step(s) described herein and may be further configured as described herein.

In the embodiment shown in FIG. 3, one of the computer systems is part of an EDA tool, and the inspection system and another of the computer systems are not part of the EDA tool. For example, as shown in FIG. 3, one of the computer systems may be computer system 302 included in EDA tool 304. The EDA tool and the computer system included in such a tool may include any commercially available EDA tool that has been modified to perform the steps described herein. Therefore, the computer system that is configured to perform the identifying and generating steps described herein may be separate from an inspection system that is used to inspect the wafer. In other words, the design may be used by one system or tool to create the altered design that will be used by another, different system or tool to perform inspection and/or binning of defects detected by inspection. The computer system that is used to create the altered design also may not be part of an EDA tool and may be included in another system or tool or simply be configured as a stand alone computer system. Furthermore, although the altered design may be generated by one tool and used by another tool, the tool or computer system that generates the altered design may be configured to provide that information to the other tool by storing or transferring the altered design to a shared computer-readable storage medium such as a fab database or by transmitting the altered design directly to the tool that will use it, which may be performed as described further herein.

The inspection system may be configured to generate the output for the layer in the device being fabricated on a wafer by scanning the wafer with light and detecting light from the wafer during the scanning. For example, as shown in FIG. 3, the inspection system includes light source 306, which may include any suitable light source known in the art. Light from the light source may be directed to beam splitter 308, which may be configured to direct the light from the light source to wafer 310. The light source may be coupled to any other suitable elements (not shown) such as one or more condensing lenses, collimating lenses, relay lenses, objective lenses, apertures, spectral filters, polarizing components and the like. As shown in FIG. 3, the light may be directed to the wafer at a normal angle of incidence. However, the light may be directed to the wafer at any suitable angle of incidence including near normal and oblique incidence. In addition, the light or multiple light beams may be directed to the wafer at more than one angle of incidence sequentially or simultaneously. The inspection system may be configured to scan the light over the wafer in any suitable manner.

Light from wafer 310 may be collected and detected by one or more channels of the inspection system during scanning. For example, light reflected from wafer 310 at angles relatively close to normal (i.e., specularly reflected light when the incidence is normal) may pass through beam splitter 308 to lens 312. Lens 312 may include a refractive optical element as shown in FIG. 3. In addition, lens 312 may include one or more refractive optical elements and/or one or more reflective optical elements. Light collected by lens 312 may be focused to detector 314. Detector 314 may include any suitable detector known in the art such as a charge coupled device (CCD) or another type of imaging detector. Detector 314 is configured to generate output that is responsive to the reflected light collected by lens 312. Therefore, lens 312 and detector 314 form one channel of the inspection system. This channel of the inspection system may include any other suitable optical components (not shown) known in the art.

Since the inspection system shown in FIG. 3 is configured to detect light specularly reflected from the wafer, the inspection system is configured as a BF inspection system. Such an inspection system may, however, also be configured for other types of wafer inspection. For example, the inspection system shown in FIG. 3 may also include one or more other channels (not shown). The other channel(s) may include any of the optical components described herein such as a lens and a detector, configured as a scattered light channel. The lens and the detector may be further configured as described herein. In this manner, the inspection system may also be configured for DF inspection.

The inspection system may also include a computer system that is configured to perform one or more steps of the methods described herein. For example, the optical elements described above may form optical subsystem 316 of inspection subsystem 300, which may also include computer system 318 that is coupled to the optical subsystem. In this manner, output generated by the detector(s) during scanning may be provided to computer system 318. For example, the computer system may be coupled to detector 314 (e.g., by one or more transmission media shown by the dashed line in FIG. 3, which may include any suitable transmission media known in the art) such that the computer system may receive the output generated by the detector.

The computer system of the inspection system may be configured to perform any step(s) described herein. For example, computer system 318 may be configured for performing the detecting and binning steps as described herein. In addition, computer system 318 may be configured to perform any other steps described herein. Furthermore, although some of the steps described herein may be performed by different computer systems, all of the steps of the method may be performed by a single computer system such as that of the inspection system or a stand alone computer system. In addition, the one or more of the computer system(s) may be configured as a virtual inspector such as that described in U.S. Pat. No. 8,126,255 issued on Feb. 28, 2012 to Bhaskar et al., which is incorporated by reference as if fully set forth herein.

The computer system of the inspection system may also be coupled to the other computer system that is not part of the inspection system such as computer system 302, which may be included in another tool such as the EDA tool described above such that computer system 318 can receive output generated by computer system 302, which may include the altered design generated by that computer system. For example, the two computer systems may be effectively coupled by a shared computer-readable storage medium such as a fab database or may be coupled by a transmission medium such as that described above such that information may be transmitted between the two computer systems.

It is noted that FIG. 3 is provided herein to generally illustrate a configuration of an inspection system that may be included in the system embodiments described herein. Obviously, the inspection system configuration described herein may be altered to optimize the performance of the inspection system as is normally performed when designing a commercial inspection system. In addition, the systems described herein may be implemented using an existing inspection system (e.g., by adding functionality described herein to an existing inspection system) such as the 29xx/28xx series of tools that are commercially available from KLA-Tencor. For some such systems, the methods described herein may be provided as optional functionality of the system (e.g., in addition to other functionality of the system). Alternatively, the system described herein may be designed "from scratch" to provide a completely new system.

Further modifications and alternative embodiments of various aspects of the invention will be apparent to those skilled in the art in view of this description. For example, methods and systems for binning defects on a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for binning defects on a wafer, comprising:

identifying areas in a design for a layer of a device being fabricated on a wafer that are not critical to yield of fabrication of the device;

generating an altered design for the layer by eliminating features in the identified areas from the design for the layer;

detecting defects on the layer using output of an inspection system; and binning the defects into groups using the altered design such that features in the altered design proximate positions of the defects in each of the groups are at least similar, wherein said identifying, said generating, said detecting, and said binning are performed by one or more computer systems.

2. The method of claim 1, wherein said identifying is performed using a design layout file for the design.

3. The method of claim 1, wherein generating the altered design comprises eliminating the features in the identified areas from a design layout file for the design thereby creating a modified design layout file and converting a file format of the modified design layout file to a different file format that can be used for the binning.

4. The method of claim 1, wherein the features in the altered design comprise features in areas of the design for the layer other than the identified areas.

5. The method of claim 1, wherein generating the altered design comprises eliminating the features in the identified areas and replacing features in areas of the design for the layer other than the identified areas with different features.

6. The method of claim 1, wherein said identifying comprises identifying the areas in the design for the layer that are not critical to the yield by applying user-defined rules to a design layout file for the design.

7. The method of claim 1, wherein said identifying comprises identifying the areas in the design for the layer that are not critical to the yield based on density of the features in different areas in the design for the layer.

8. The method of claim 1, wherein said identifying comprises identifying the areas in the design for the layer that are not critical to the yield based on dimensions of spaces between the features in different areas of the design for the layer.

9. The method of claim 1, wherein said identifying comprises identifying the areas in the design for the layer that are not critical to the yield based on dimensions of the features in different areas of the design for the layer.

10. The method of claim 1, wherein said identifying comprises identifying the areas in the design for the layer that are not critical to the yield based on function of the features in the different areas of the design for the layer.

11. The method of claim 1, wherein the altered design does not comprise care areas.

12. The method of claim 1, wherein the method does not comprise generating care areas for the design, the altered design, or the wafer.

13. The method of claim 1, wherein the one or more computer systems that perform said identifying and said generating comprise a computer system of an electronic design automation (EDA) tool.

14. The method of claim 1, wherein the one or more computer systems that perform said detecting and said binning comprise a computer system of the inspection system.

15. The method of claim 1, wherein, in said binning, the defects having positions that are not proximate any of the features in the altered design are not binned into any of the groups.

16. The method of claim 1, wherein said detecting is performed without regard to position of the output of the inspection system with respect to the altered design.

17. The method of claim 1, wherein information about which of the areas in the layer are not critical to the yield is not used for said detecting or said binning.

18. The method of claim 1, wherein the altered design does not comprise information for criticality of the areas in the design for the layer.

19. The method of claim 1, wherein the inspection system is a light-based inspection system.

20. A non-transitory computer-readable medium, storing program instructions executable on a computer system for performing a computer-implemented method for binning defects on a wafer, wherein the computer-implemented method comprises:

identifying areas in a design for a layer of a device being fabricated on a wafer that are not critical to yield of fabrication of the device;

generating an altered design for the layer by eliminating features in the identified areas from the design for the layer;

detecting defects on the layer using output of an inspection system; and binning the defects into groups using the altered design such that features in the altered design proximate positions of the defects in each of the groups are at least similar.

21. A system configured to bin defects on a wafer, comprising:

an inspection system configured to generate output for a layer in a device being fabricated on a wafer; and one or more computer systems configured for:

identifying areas in a design for the layer that are not critical to yield of fabrication of the device;

generating an altered design for the layer by eliminating features in the identified areas from the design for the layer;

detecting defects on the layer using the output of the inspection system; and binning the defects into groups using the altered design such that features in the altered design proximate positions of the defects in each of the groups are at least similar.

* * * * *